United States Patent [19]

Comar et al.

[11] 4,333,911

[45] Jun. 8, 1982

[54] METHOD OF PREPARING A SOLUTION OF GALLIUM 68 FROM GERMANIUM 68

[75] Inventors: Dominique Comar, Bures sur Yvette; Christian Loc'h, Rosny sous Bois; Bernard Maziere, Gif-sur-Yvette, all of France

[73] Assignee: Commissariat a l'Energie Atomique, Paris, France

[21] Appl. No.: 143,106

[22] Filed: Apr. 23, 1980

[30] Foreign Application Priority Data

Apr. 24, 1979 [FR] France ............................... 79 10361

[51] Int. Cl.³ ....................... C01G 15/00; A61K 43/00

[52] U.S. Cl. ................................. 423/2; 250/432 PD; 424/1

[58] Field of Search ............................ 424/1; 423/213; 252/645; 250/432 PD

[56] References Cited

U.S. PATENT DOCUMENTS 4,248,730 2/1981 Mirzadeh et al. ........................ 423/2
4,264,468 4/1981 Neirincky et al. ...................... 424/1

*Primary Examiner*—Christine M. Nucker

[57] ABSTRACT

A method of preparing a solution of gallium 68 from germanium 68, wherein the germanium 68 is fixed on particles of tin dioxide and the gallium 68 produced by radioactive decay of the germanium 68 fixed on said particles is then eluted with a solution of hydrochloric acid.

5 Claims, 4 Drawing Figures

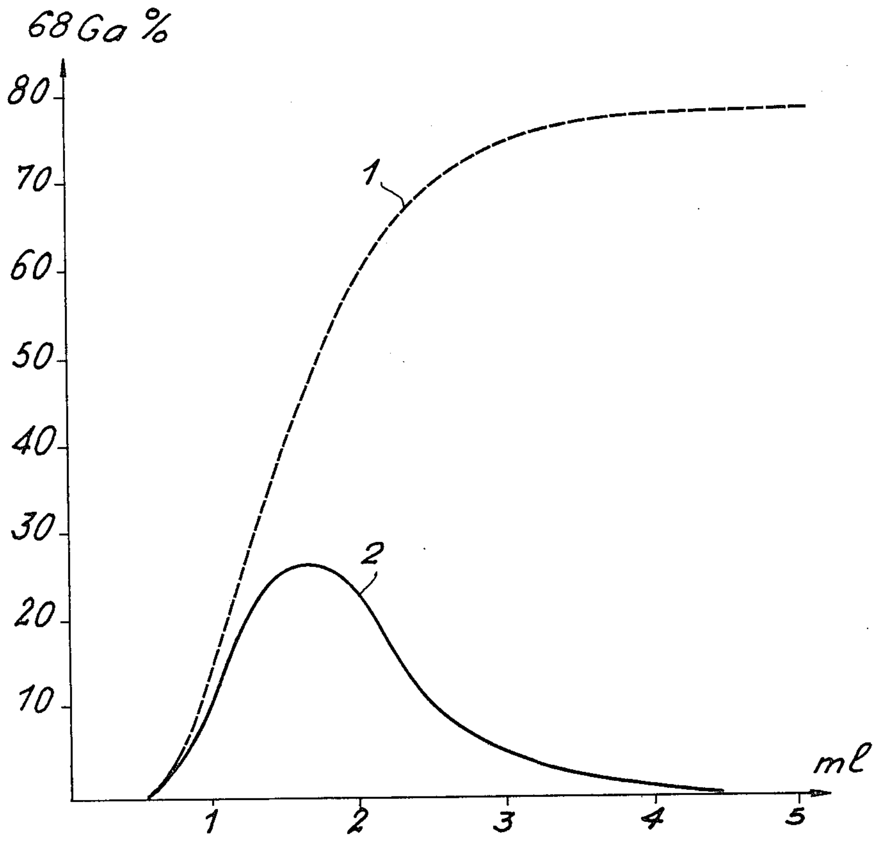
FIG. 3
FIG. 4
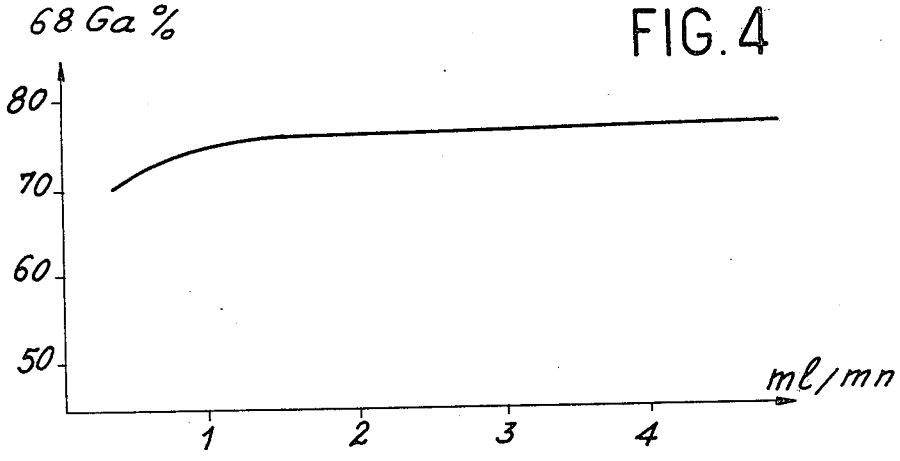

METHOD OF PREPARING A SOLUTION OF GALLIUM 68 FROM GERMANIUM 68

BACKGROUND OF THE INVENTION

The present invention relates to a method of preparing a solution of gallium 68 in ionic form, which can be used directly in the medical field for preparing labelled pharmaceutical compositions intended for making certain clinical diagnoses, in particular, by techniques of tomography by positron emission.

It is known that positron emitters occupy a special place amongst the radioelements which can be used in nuclear medicine, since they lead to the coincident emission of two gamma photons, with which it is possible to obtain good quality tomographic images.

Radioelements of this kind generally have very short half-lives, which is an advantage from the point of view of dosimetry but presents certain problems in the clinical use of these radioelements in hospital centres which do not have the considerable facilities needed for their production.

Of these radioelements, gallium 68 is of great interest as it is a positron emitter with a half-life of 68.3 min., which is produced during the decay by electronic capture of germanium 68, which has a half-life of 280 days.

Thus, if it is possible to separate the daughter element gallium 68 from the parent element germanium 68, it is possible to produce an autonomous source of positron emitter with a short half-life, which decays only very slowly in the course of time owing to the long half-life of germanium 68, and which can be used several times a day, since the equilibrium between germanium 68 and gallium 68 is achieved in a few hours.

Up to now, the methods used for obtaining gallium 68 from germanium 68 have made use of extraction techniques using a solvent or chromatographic techniques.

In solvent extraction methods, gallium 68 is extracted in an organic solvent, for example in the form of a complex of acetyl acetone when the organic solvent is cyclohexane, or in the form of a 68 Ga-oxine complex when the organic solvent is chloroform.

In the separation processes using a chromatographic technique, germanium 68 can be fixed on a column of alumina and then the column can be eluted with a solution of ethylenediamine tetraacetic acid 0.005 M (EDTA) to recover the gallium 68.

These known processes have certain disadvantages. In fact, the processes which use a solvent extraction step lead to gallium solutions wherein the gallium is obtained in a sequestered form which cannot be used directly for labelling pharmaceutical preparations and therefore has to undergo additional treatments, generally resulting in a reduction in the available radioactivity. Moreover, during extraction by solvent, it is difficult to automate the separation of the aqueous and organic phases, with the result that there are considerable risks of irradiation and contamination.

The methods using chromatographic techniques do not produce very high yields of gallium 68; moreover, this yield decreases substantially as a function of time and again the gallium is obtained in sequestered form.

BRIEF SUMMARY OF THE INVENTION

The present invention relates precisely to a method of preparing a solution of gallium 68 which remedies the disadvantages of the methods mentioned above.

The method according to the invention for preparing a solution of gallium 68 from germanium 68 is characterised in that it consists in fixing the germanium 68 on particles of tin dioxide, and then eluting the gallium 68 produced by radioactive decay of the germanium 68 fixed on these particles, using a solution of hydrochloric acid.

According to the invention, the germanium 68 is advantageously fixed on the tin dioxide particles by causing a solution of hydrochloric acid containing germanium 68 to circulate in a column filled with these tin dioxide particles.

According to an advantageous feature of the process of the invention, the hydrochloric acid solution used to fix the germanium 68 on the particles of tin dioxide has a concentration of hydrochloric acid of between 0.5 and 4 N.

According to a further feature of the process of the invention, the hydrochloric acid solution used to extract the gallium 68 by eluting the particles has a concentration of hydrochloric acid of between 1 N and 2 N.

Advantageously, the hydrochloric acid solutions used to fix the germanium 68 and to extract the gallium 68 have the same concentration of hydrochloric acid, preferably a concentration of about 1 N.

In particular, the method of the invention has the advantage of producing a solution of gallium 68 in ionic form, which can be used directly for labelling pharmaceutical compositions, for example for tagging microspheres of human albumen serum or for preparing gallium 68 citrate or pyrophosphate.

Moreover, the use of tin dioxide particles makes it possible to fix the germanium 68 permanently and quantitatively, and to achieve satisfactory separation of the gallium 68 produced by radioactive decay of the germanium 68.

In fact, by eluting tin dioxide particles with hydrochloric acid, a very pure solution of gallium 68 is obtained, with a high yield of gallium 68, even when elution is carried out very rapidly.

BRIEF DESCRIPTION OF THE DRAWINGS

The invention will be more fully understood from the following description, with reference to the accompanying drawings, wherein:

FIG. 3 is a graph showing the variations in the percentage of gallium 68 eluted as a function of the quantity (in ml) of hydrochloric acid used for the elution; and FIG. 4 is a graph showing the variations in the percentage of gallium 68 eluted as a function of the flow rate (in ml/min) of the HCl solution used for elution.

DETAILED DESCRIPTION OF THE PREFERRED EMBODIMENTS

Figure 1:
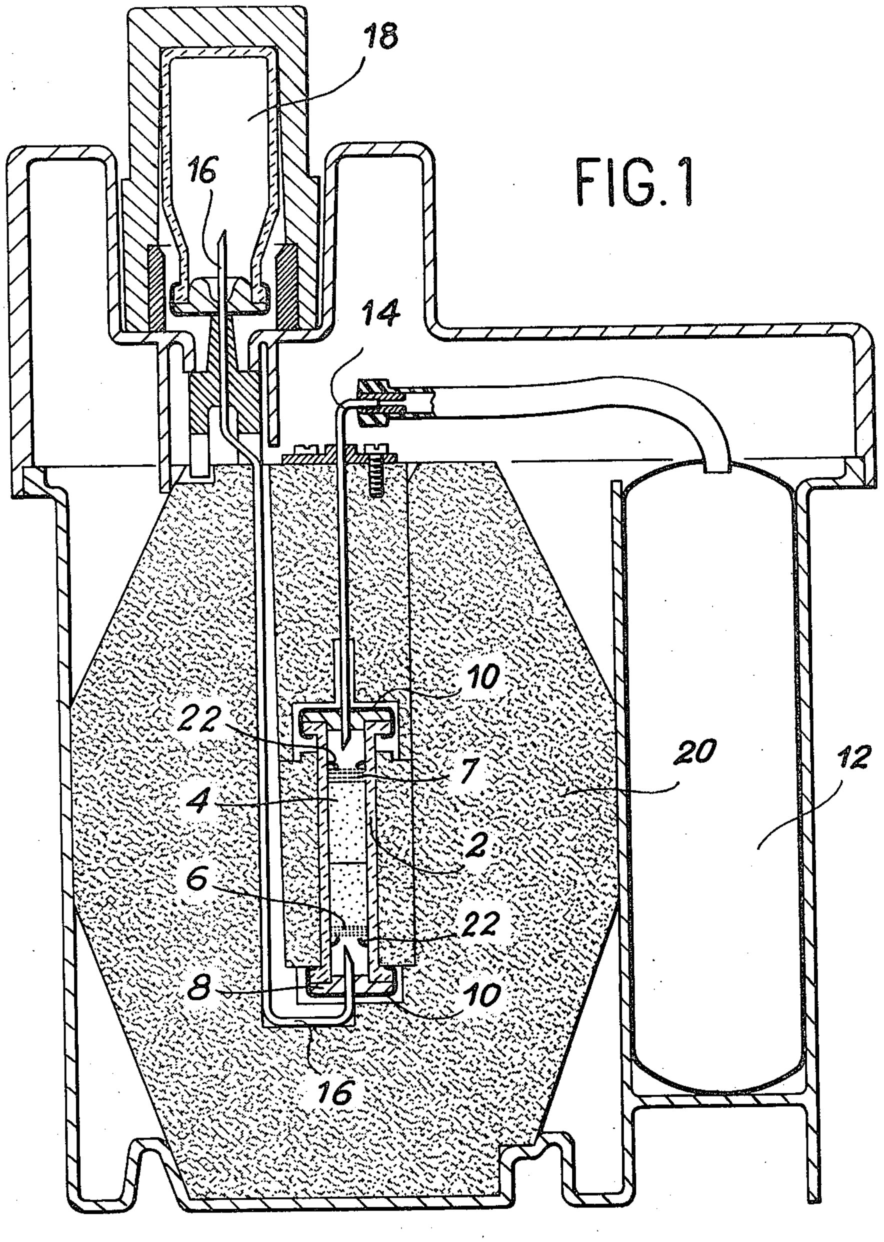
FIG. 1 is a vertical section through a generator of gallium 68 for performing the method of the invention.

Referring to FIG. 1, it will be seen that the generator of gallium 68 consists of a glass column 2, having an internal diameter of 10 mm and a height of 15 mm, for example, in which there are particles of tin dioxide 4 which are held in at the bottom by a sintered glass 6 and at the top by a plug of glass wool 7 locked in place by a polyethylene ring 22. The column 2 is closed off at both ends by rubber stoppers 8 held in place by metal caps 10.

A reservoir 12 containing the eluant solution is connected by a platinum needle 14 to the top of the column 2; at its bottom, the column 2 is connected by an outlet needle 16 to a flask 18 intended to receive the eluate from the column, this flask 18 being replaced, between two elution processes, by a flask containing a bacteriostatic agent to maintain the sterility of the generator.

The column 2 and the needles 14 and 16 are protected by lead armour-plating bearing the reference numeral 20.

In the method according to the invention, first of all the germanium 68 is fixed on the particles 4 of tin dioxide by causing a hydrochloric acid solution containing germanium 68 and non-radioactive germanium, used as the entrainer, to circulate in the column 2. For example, 50 ml of a 1 N hydrochloric acid solution containing 10 millicuries of germanium 68 and 100 micrograms of entraining germanium can be used to fix the germanium 68 on columns containing 2 g, 3 g or 5 g of tin dioxide, for example powdered tin dioxide such as that produced by Carlo ERBA of Milan (Italy), this powdered tin dioxide previously having been freed from the very fine particles by successively putting it into suspension and decanting it into a 1 N hydrochloric acid solution several times.

At the end of the operation, the column contains about 1 ml of hydrochloric acid and virtually all the germanium 68 put in. In fact, it was found that the germanium 68 contents of the hydrochloric acid solutions leaving the column 2 containing 2 g, 3 g or 5 g of tin dioxide, are 3°/oo, 0.2°/oo and 0.1°/oo, respectively. Thus, a column containing 3 g of tin dioxide fixes 99.9% of the germanium 68 put in.

After the germanium 68 has been fixed on the tin dioxide particles, the generator is eluted, by causing the desired quantity of hydrochloric acid used as eluent, e.g. 5 ml, to circulate in the column 2, and collecting in the flask 18 the eluate which contains the gallium 68 produced in the column 2 by radioactive decay of the germanium 68 fixed on the particles 4 of tin dioxide.

A number of elutions are carried out, varying the hydrochloric acid concentration of the eluent and the elution flow rate, which can be adjusted to the desired rate by any suitable means (not shown in the drawing).

The activity of the eluates collected in the flasks 18 is determined, using an ionisation chamber. In addition, various analyses of these eluates are carried out in order to verify:

their germanium 68 content, which is measured by means of an NaI(TI) scintillator by the gallium 68 present in the eluate, 48 hours after the end of elution, and their chemical purity, which is determined by neutron activation, by subjecting 100 microliters of eluate to irradiation for 18 hours in a nuclear reactor under a thermal neutron flux of $3\times10^{13}$n $cm^{-2}s^{-1}$ and detecting the radioactivity induced by means of a Ge(Li) diode after periods of decay ranging from one week to one month.

Figure 2:
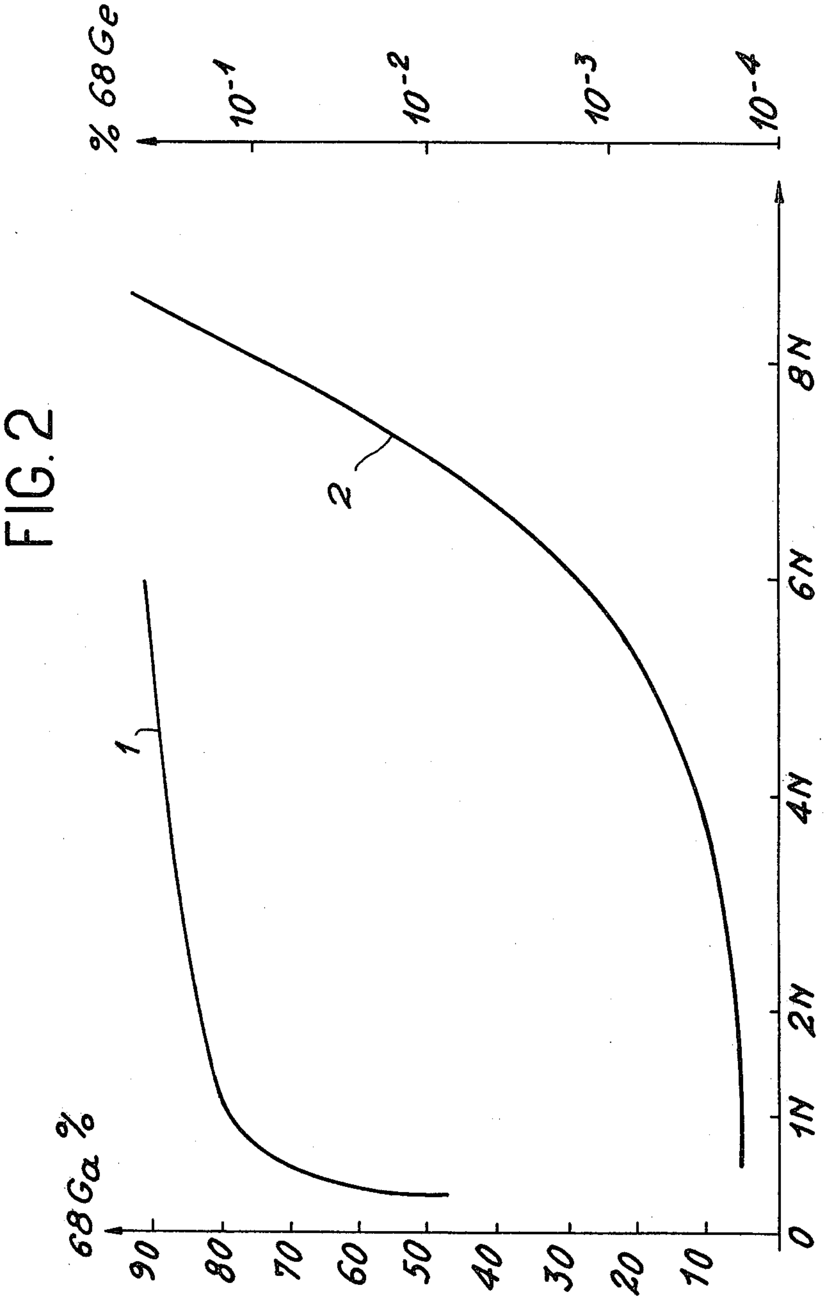
FIG. 2 is a graph showing the variations in the percentage of gallium 68 and germanium 68 eluted from the generator as a function of the acidity of the hydrochloric acid solution used for elution.

The results obtained are given in FIGS. 2 to 4.

Referring to FIG. 2, which illustrates the effect of the acidity of the hydrochloric acid solution used for elution on the percentage of gallium 68 extracted in 5 ml of eluate (curve 1) and on the contamination with germanium 68 (curve 2) defined by the percentage of germanium 68 extracted in 5 ml of eluate, it is found that the elution yield of gallium 68 increases with the acidity of the eluant and that the contamination with germanium 68 also increases with the acidity of the eluent, and indeed increases more rapidly than the elution yield.

Thus, it appears that a 1 N hydrochloric acid solution which will elute more than 78% of the gallium 68 present in the generator and less than 0.0002% of the germanium 68 fixed in the generator is the most favourable compromise.

Referring to FIG. 3, which shows the elution yield of gallium 68 in a column containing 3 g of tin dioxide, as a function of the quantity (in ml) of 1 N hydrochloric acid solution used for the elution, it will be seen that 75% of the gallium 68 activity of the generator in equilibrium can be recovered in 2.5 ml of eluate (curve 1).

However, by studying curve 2, which shows the percentage of gallium 68 recovered in each fraction of 0.5 ml of eluent as it passes through the column, we see that the gallium recovery is at its maximum when the third fraction of 0.5 ml of eluent passes through.

Referring to FIG. 4, which shows the variations of the percentage of gallium 68 extracted in the eluant solution (HCl 1 N) as a function of the elution flow rate (in ml/min), it is found that the elution yield is independent of the flow rate of eluent through the column. In fact, the 5% reduction observed at a flow rate of 0.4 ml/min is caused solely by the radioactive decay of the gallium during the 12 minutes taken to carry out elution with 5 ml of hydrochloric acid solution.

To simulate the use of a generator of this kind twice a day for a year, volumes of 1 N hydrochloric acid equivalent to 500 elutions of 5 ml are passed through the column 2 containing 3 g of tin dioxide, on which 10 millicuries of germanium 68 have been fixed, as hereinbefore.

By measuring the activities eluted every 10 elutions up to the 100th and every 50 elutions up to the 500th, it is found that, after 500 elutions, the yield of gallium 68 is even greater than 74%. Moreover, analysis of the eluates obtained shows that the chemical purity of the eluates is not impaired by intensive use of the generator. In fact, the results of these analyses, given in the following table for the second and 500th elutions, show that the quantity of tin present in 5 ml of eluate remains constant and negligible (about 0.5 μg/ml); the same applies to the other metallic impurities, which originate mainly from the acid used as eluent.

TABLE 1

Masses (μg) of metallic contaminants measured in 5 ml of 1N HCl eluate by neutron activation.

| | Sn | Ba | Co | Cr | Fe | Hg | Sb | Zn |
|---|---|---|---|---|---|---|---|---|
| 1N HCl | — | 0.04 | 0.01 | 0.01 | 0.9 | 0.004 | — | 0.8 |
| Eluate no. 2 | 2.5 | 0.12 | 0.02 | 0.05 | 0.9 | 0.01 | 0.004 | 0.6 |
| Eluate no. 500 | 2.7 | 0.03 | 0.02 | 0.01 | 0.8 | 0.005 | — | 0.8 |

Thus, it will be seen that there is no solubilisation of the tin dioxide in the hydrochloric acid solution used for the elution. Moreover, this very slight contamination with tin can be regarded as negligible, as it is known that some 500 micrograms of tin are normally added to the injectable preparation in order to promote the attachment of radioelements to microspheres of albumen serum.

Finally, tests are carried out to ensure that the autoirradiation phenomena of the eluant solution of hydrochloric acid do not lead to a reduction in the elution yield and/or excessive contamination of the eluate with germanium 68 and various impurities.

For this purpose, generators of 10μ Ci of germanium 68 are exposed to external irradiation, for example by placing them at different distances from sources of cobalt 60 so as to obtain dosage flow rates corresponding to the dose which accumulates to the liquid phase of the generator during the 5 hours or 80 hours following an elution. These doses were calculated by comparing a humid generator impregnated with eluent with a homogeneous system, using the following formula:

$$D=C(B+gG)$$

wherein C is the mass activity of the generator,
B is the deposited energy coming from the positrons,
G is the energy coming from the various electromagnetic radiations, and
g is the fraction of G actually deposited in the system.

For a generator 10 mm in diameter and 15 mm high, containing 3 g of tin dioxide which holds about 1 ml of eluent, the autoradiographs show that the germanium 68 is actually only fixed to the top two-thirds of the column of tin dioxide particles.

Using the following values:
$B=1.573$ krad $h^{-1}$/mCi $g^{-1}$ for $^{68}Ga$
$G=2.055$ krad $h^{-1}$/mCi $g^{-1}$ for the combination of $^{68}Ge$-$^{68}Ga$
$g=0.135$
it is found that for a moist generator of 20 millicuries of gallium 68 in equilibrium, impregnated with 1 N hydrochloric acid, the flow rate of dose absorbed by the liquid phase is approximately 12 krad $h^{-1}$, and by integrating as a function of time it is found that the doses accumulated by the liquid phase in the 5 hours and 80 hours after an elution (75% yield) are approximately 50 kilorads and approximately 1 megarad, respectively.

Under these conditions, the measurements made with the eluates collected before and after irradiation of the generator show that the elution yield and contamination of the eluate with germanium 68 and other impurities are unchanged.

Thus, with the method according to the invention, it is possible to obtain, by elution of a gallium 68 generator containing 5 millicuries of gallium 68, 5 ml of 1 N HCl containing 4 mCi of $^{68}Ga$ in 1.5 minutes, in which case the elution yield is about 80%.

Under these conditions, the germanium 68 activity (12 nanocuries) of the eluate remains less than 0.0003% of the fixed germanium activity.

This gallium 68 generator constitutes a definite improvement in the conditions for producing gallium 68.

In fact, ionic gallium 68 is obtained in less than 2 min., whereas it takes at least 30 min. in the systems which use extraction by solvent or chromatography on an alumina column.

Elution can be carried out with virtually a full yield every 3 to 4 hours.

The extraction yield of gallium 68 is high (78 to 80%) and greater than that of a generator using the alumina/ethylenediamine tetraacetic acid system (yield 70%). Moreover, this yield is not subject to autoirradiation.

The contamination of the eluate with germanium 68 is limited (less than 0.0003% by elution) and in any case it is 10 times less than the contamination obtained with an $Al_2O_3$ EDTA or oxine generator.

This low level of germanium 68 in the eluate causes only negligible additional irradiation of the patient. In fact, the 12 nanocuries of germanium 68 contaminating the 4 millicuries of gallium 68 eluted from the generator constitute only 1/40th of the dose received in the liver.

After a year's intensive use, the germanium 68 activity eluted from the tin dioxide/hyrochloric acid generator is still more than 70% of the available activity.

Finally, this generator can be made in the form of a sterile apparatus, since the use of a partial vacuum to accelerate elution does not affect the gallium yield of the generator, and this yield remains constant when elution is carried out at reduced pressure. By contrast, when using gallium generators of the $Al_2O_3$/EDTA type, the quantity of gallium 68 available in the eluate decreases when the elution flow rate is increased, and the use of a partial vacuum to accelerate elution results in a substantial reduction in the activity in available gallium 68; this reduction may be as much as 60%.

The solutions of gallium 68 in ionic form obtained with a generator of this kind can be used for tagging microspheres of human albumen serum by conventional methods, with a yield of 80%, after the eluate obtained has been neutralised to pH 2.

Similarly, the citrate and pyrophosphate derivatives of gallium 68, identified by chromatography on paper, can be prepared from the neutralised eluate.

The invention is not limited to the embodiments described and represented hereinbefore and various modifications can be made thereto without passing beyond the scope of the invention.

What is claimed is:

1. A method of preparing a solution of gallium 68 from germanium 68, wherein the germanium 68 is fixed on particles of tin dioxide and the gallium 68 produced by radioactive decay of the germanium 68 fixed on said particles is then eluted with a solution of hydrochloric acid.

2. A method according to claim 1, wherein the germanium 68 is fixed on said tin dioxide particles by causing a solution of hydrochloric acid containing germanium 68 to circulate in a column filled with said tin dioxide particles.

3. A method according to claim 2, wherein the hydrochloric acid solution used to fix the germanium 68 on the tin dioxide particles has a hydrochloric acid concentration of between 0.5 and 4 N.

4. A method according to claim 1, wherein the hydrochloric acid solution used to elute the gallium 68 has a hydrochloric acid concentration of between 1 N and 2 N.

5. A method according to claim 2, wherein the hydrochloric acid solutions used to fix the germanium 68 and extract the gallium 68 have a hydrochloric acid concentration of about 1 N.

* * * * *